US007148211B2

(12) United States Patent
Mazess et al.

(10) Patent No.: US 7,148,211 B2
(45) Date of Patent: Dec. 12, 2006

(54) FORMULATION FOR LIPOPHILIC AGENTS

(75) Inventors: Richard B. Mazess, Madison, WI (US); Jeffrey W. Driscoll, Middleton, WI (US); Creighton Reed Goldensoph, DeForest, WI (US); Leon W. LeVan, Oregon, WI (US)

(73) Assignee: Genzyme Corporation, Cambridge, MA (US)

( * ) Notice: Subject to any disclaimer, the term of this patent is extended or adjusted under 35 U.S.C. 154(b) by 361 days.

(21) Appl. No.: 10/247,765

(22) Filed: Sep. 18, 2002

(65) Prior Publication Data

US 2004/0053894 A1    Mar. 18, 2004

(51) Int. Cl.
*A01N 45/00* (2006.01)
*A61K 31/59* (2006.01)

(52) U.S. Cl. .................................. 514/168; 514/167
(58) Field of Classification Search ................ 514/167, 514/168
See application file for complete search history.

(56) References Cited

U.S. PATENT DOCUMENTS

| | | | |
|---|---|---|---|
| 2,383,446 A | 6/1945 | Calcott et al. | |
| 3,697,559 A | 10/1972 | DeLuca et al. | |
| 3,741,996 A | 6/1973 | DeLuca et al. | |
| 3,907,843 A | 9/1975 | DeLuca et al. | |
| 3,932,634 A | 1/1976 | Kardys | |
| 4,075,333 A | 2/1978 | Josse | |
| 4,160,803 A | 7/1979 | Potts | |
| 4,195,027 A | 3/1980 | DeLuca et al. | |
| 4,202,829 A | 5/1980 | DeLuca et al. | |
| 4,225,596 A | 9/1980 | DeLuca | |
| 4,234,495 A | 11/1980 | DeLuca et al. | |
| 4,260,549 A | 4/1981 | DeLuca et al. | |
| 4,308,264 A | 12/1981 | Conway | |
| 4,362,710 A | 12/1982 | Watanabe | |
| 4,364,941 A | 12/1982 | Kiyoki et al. | |
| 4,391,802 A | 7/1983 | Suda et al. | |
| 4,508,651 A | 4/1985 | Baggiolini et al. | |
| 4,554,106 A | 11/1985 | DeLuca et al. | |
| 4,555,364 A | 11/1985 | DeLuca et al. | |
| 4,588,716 A | 5/1986 | DeLuca et al. | |
| 4,661,294 A | 4/1987 | Holick et al. | |
| 4,689,180 A | 8/1987 | DeLuca et al. | |
| 4,698,328 A | 10/1987 | Neer et al. | |
| 4,717,721 A | 1/1988 | DeLuca et al. | |
| 4,727,064 A | 2/1988 | Pitha | |
| 4,784,845 A | 11/1988 | Desai | |
| 4,816,247 A | 3/1989 | Desai | |
| 4,833,125 A | 5/1989 | Neer et al. | |
| 4,866,048 A | 9/1989 | Calverley et al. | |
| 4,877,778 A | 10/1989 | Carpenter | |
| 4,902,481 A | 2/1990 | Clark et al. | |
| 4,948,788 A | 8/1990 | Makino | |
| 4,948,789 A | 8/1990 | Slatopolsky | |
| 5,063,221 A | 11/1991 | Nishii et al. | |
| 5,085,864 A | 2/1992 | Cannon | |
| 5,092,840 A | 3/1992 | Healy | |
| 5,104,864 A | 4/1992 | DeLuca | |
| 5,120,720 A | 6/1992 | Pitha | |
| 5,124,152 A * | 6/1992 | Biringer et al. ............. 424/422 |
| 5,134,127 A | 7/1992 | Stella | |
| 5,141,719 A | 8/1992 | Fernwood et al. | |
| 5,157,135 A | 10/1992 | Tsuji et al. | |
| 5,158,944 A | 10/1992 | Makino | |
| 5,182,274 A | 1/1993 | Makino | |
| 5,205,989 A | 4/1993 | Aysta | |
| 5,219,528 A | 6/1993 | Clark | |
| 5,232,836 A | 8/1993 | Bouillon et al. | |
| 5,260,290 A | 11/1993 | DeLuca et al. | |
| 5,264,184 A | 11/1993 | Aysta et al. | |
| 5,264,618 A | 11/1993 | Felgner et al. | |
| 5,298,246 A | 3/1994 | Yano | |
| 5,334,740 A | 8/1994 | Takahashi et al. | |
| 5,338,532 A | 8/1994 | Tomalia et al. | |
| 5,360,413 A | 11/1994 | Leason et al. | |
| 5,366,965 A | 11/1994 | Strein | |
| 5,372,996 A | 12/1994 | Labrie | |
| 5,376,645 A | 12/1994 | Stella | |
| 5,403,831 A | 4/1995 | DeLuca | |
| 5,417,923 A | 5/1995 | Bojanic et al. | |
| 5,474,923 A | 12/1995 | Takeda | |
| 5,487,900 A | 1/1996 | Itoh | |
| 5,488,120 A | 1/1996 | Knutson et al. | |
| 5,527,524 A | 6/1996 | Tomalia et al. | |
| 5,532,229 A | 7/1996 | Vieth | |
| 5,549,577 A | 8/1996 | Siegel et al. | |
| 5,554,386 A | 9/1996 | Groman et al. | |
| 5,561,123 A | 10/1996 | DeLuca | |
| 5,565,442 A | 10/1996 | Silver | |
| 5,597,575 A | 1/1997 | Breitbarth | |
| 5,602,116 A | 2/1997 | Knutson | |
| 5,614,513 A | 3/1997 | Knutson et al. | |

(Continued)

FOREIGN PATENT DOCUMENTS

BE    877 356    10/1979

(Continued)

OTHER PUBLICATIONS

Aloia, J. et al., *Amer. J. Med.*, (1988) 84:401-08.

(Continued)

*Primary Examiner*—Sreeni Padmanabhan
*Assistant Examiner*—G. Mitchell
(74) *Attorney, Agent, or Firm*—Jeffrey D. Peterson; Michael Best & Friedrich LLP

(57) ABSTRACT

The invention relates to pharmaceutical formulations of lipophilic therapeutic agents in which such agents are solubilized in largely aqueous vehicles, and processes for preparing and using the same.

6 Claims, No Drawings

U.S. PATENT DOCUMENTS

| | | | |
|---|---|---|---|
| 5,632,315 A | 5/1997 | Rose | |
| 5,637,742 A | 6/1997 | Valles et al. | |
| 5,645,856 A | 7/1997 | Lacy | |
| 5,661,025 A | 8/1997 | Szoka, Jr. et al. | |
| 5,668,174 A | 9/1997 | Kawagishi | |
| 5,691,328 A | 11/1997 | Peterson et al. | |
| 5,716,346 A | 2/1998 | Farris | |
| 5,739,271 A | 4/1998 | Sridhar et al. | |
| 5,763,428 A | 6/1998 | Knutson | |
| 5,763,429 A | 6/1998 | Bishop | |
| 5,766,582 A | 6/1998 | Yuen et al. | |
| 5,795,882 A | 8/1998 | Bishop et al. | |
| 5,798,345 A | 8/1998 | Knutson | |
| 5,804,573 A | 9/1998 | Silver | |
| 5,817,648 A | 10/1998 | Kutner | |
| 5,827,883 A * | 10/1998 | Barbier et al. | 514/546 |
| 5,858,999 A | 1/1999 | Su | |
| 5,869,386 A | 2/1999 | Hamajima | |
| 5,874,418 A | 2/1999 | Stella | |
| 5,880,114 A | 3/1999 | DeLuca | |
| 5,932,544 A * | 8/1999 | Grinna | 514/12 |
| 5,939,407 A | 8/1999 | Landfield | |
| 5,965,160 A | 10/1999 | Benita | |
| 5,972,917 A | 10/1999 | Bishop | |
| 6,045,538 A | 4/2000 | Farris | |
| 6,046,177 A | 4/2000 | Stella | |
| 6,051,567 A | 4/2000 | Abrahamson | |
| 6,096,338 A | 8/2000 | Lacy | |
| 6,136,799 A | 10/2000 | Li | |
| 6,171,603 B1 | 1/2001 | Bernardon | |
| 6,211,169 B1 | 4/2001 | Shinal | |
| 6,245,776 B1 | 6/2001 | Skwierczynski et al. | |
| 6,294,192 B1 | 9/2001 | Patel | |
| 6,294,548 B1 | 9/2001 | James | |
| 6,361,758 B1 | 3/2002 | Li | |
| 6,406,455 B1 | 6/2002 | Willis et al. | |
| 6,417,177 B1 | 7/2002 | Nelson | |
| 6,436,430 B1 | 8/2002 | Mulye | |
| 6,503,893 B1 | 1/2003 | Bishop et al. | |
| 6,521,608 B1 | 2/2003 | Henner et al. | |
| 6,537,982 B1 | 3/2003 | Bishop et al. | |
| 6,538,037 B1 | 3/2003 | Bishop et al. | |

FOREIGN PATENT DOCUMENTS

| | | |
|---|---|---|
| EP | 0197514 | 10/1986 |
| EP | 0390097 | 10/1990 |
| EP | 0503630 | 9/1992 |
| EP | 0562497 | 9/1993 |
| EP | 0664287 | 7/1995 |
| JP | 62000033 | 10/1986 |
| JP | 5320127 | 9/1993 |
| JP | 6025039 | 2/1994 |
| WO | WO 84/04527 | 11/1984 |
| WO | WO 87/00834 | 2/1987 |
| WO | WO 90/10620 | 9/1990 |
| WO | WO 92/05130 | 4/1992 |
| WO | WO 92/12165 | 7/1992 |
| WO | WO 92/21355 | 12/1992 |
| WO | WO 93/07883 | 4/1993 |
| WO | WO 93/14763 | 8/1993 |
| WO | WO 94/16711 | 8/1994 |
| WO | 96/36340 | 5/1996 |
| WO | WO 96/31215 | 10/1996 |
| WO | WO 96/40153 | 12/1996 |
| WO | WO 99/49870 | 10/1999 |
| WO | 00/61112 | 4/2000 |
| WO | WO 01/07075 | 2/2001 |
| WO | 02/15894 | 8/2001 |
| WO | WO 01/68017 | 9/2001 |
| WO | WO 02/34198 | 5/2002 |

OTHER PUBLICATIONS

Barton, D. et al., "Synthetic Uses of Steroidal Ring & Diene Protection: 22,23-Dihydroergosterol," *JCS Perkin I*, (1976) pp. 821-826.

Beer, et al., "A Phase I Trial of Pulse Calcitriol in Patients with Refractory Malignancies," *Cancer*, (Jun. 15, 2001) 91:12:2431-2439.

Beer, et al., "Weekly High-Dose Calcitriol and Docetaxel in Advanced Prostate Cancer," *Seminars in Oncology*, Suppl 15 (Aug. 2001) 28:4:49-55.

Beer, T. et al., "Weekly High-Dose Calcitriol and Docetaxel in Metastatic Androgen-Independent Prostate Cancer," *Journal of Clinical Oncology*, (Jan. 2003) 21:1:123-128.

Blazsek, I. et al. "Combined Differentiation Therapy in Myelodysplastic Syndrome with Retinoid Acid, 1α,25 Dihydroxyvitamin $D_3$, and Prednisone," 16:4:259-264 (Abstract).

Brautbar, N. "Osteoporosis: Is 1,25-(OH)2D3 of Value in Treatment?" *Nephron* (1986) 44:161-166.

Braunwald, E. et al., *Harrison's Principles of Internal Medicine*: Part Eleven, "Disorders of Bone and Mineral Metabolism," Chapter 335, McGraw-Hill, New York, (1987) pp. 1860-1865.

Brown, J.P. et al., "Serum Bone Gala-Protein: A Specific Marker for Bone Formation in Postmenopausal Osteoporosis," *Lancet*, (1984) 1:1091-1093.

Caniggia, A. et al., "Effect of a Long-Term Treatment with 1,25-Dihydroxyvitamin $D_3$ on Osteocalcin in Postmenopausal Osteoporosis," *Cacified Tissue Int.*, (1986) 38:328-332.

Christiansen, C. et al., "Prevention of Early Postmenopausal Bone Loss: Controlled 2-Year Study in 315 Normal Females," *Europ J Clin Inves.*, (1980) 10:273-279.

Christiansen, C. et al., *Eur. J. Clin.* Invest., (1981) 11:305-309.

Crump, D.R. et al., "(22S)-Hydroxyvitamin $D_4$," *J.C.S. Perkins Trans. I*, (1973) pp. 2731-2733.

Cho, Y.L. et al., "Combined Effects of 1,25-Dihydroxyvitamin $D_3$ and Platinum Drugs on the growth of MCF-7 Cells," *Cancer Research*, (Jun. 1991) 51:2848-2853.

Defacque, H. et al., "Different Combinations of Retinoids and Vitamin $D_3$ Analogs Efficiently Promote Growth Inhibition and Differentiation of Myelomonocytic Leukemia Cell Lines," *J. Pharmacology and Experimental Therapeutics*, (1994) 271:193-199.

DeLuca et al., "Synthesis, Biological Activity, and Metabolism of 22,23-$^3$H-Vitamin $D_4$," *Arch. Biochem, Biophys.*, (1968) 124:122-128.

Duda et al., "1,25-Dihydroxyvitamin D Stimulation Test for Osteoblast Function in Normal and Osteoporotic Postmenopausal Women," *J. Clinic Inves.*, (1987) 79:1249-1253.

Endo, K. et al., "Effect of Combination Treatment with Vitamin D Analog (OCT) and a Biophosphonate (AHPrBP) in a Nude Mouse Model of Cancer-Associated Hypercalcemia," *Journal of Bone and Mineral Research*, (1998) 13:9:1378-1383.

Foldes, J. et al., "Long Term Treatment with 1α (OH)$D_3$ for Postmenopausal Osteoporosis: Efficacy and Safety," *Osteoporosis*, (1987) 2:971-973.

Gallagher, J.C., et al., *Annals of Int. Med.*, (1990) 13:649-655.

Gallagher, J.C. et al., "Effects of Increasing Doses of 1α-Hydroxyvitamin $D_2$ on Calcium Homeostasis in Postmenopausal Osteopenic Women," *J. Bone Min. Res.*, (1994) 9:607-614.

Grab, W. *Z. Physiol. Chem.*, (1936) 243:63-89.

Guidelines for the Clinical Evaluation of Drugs Used in the Treatment of Osteoporosis, HEW (FDA) 80-3094, (1979) pp. 5-6.

Hershberger, P. et al. "Calcitriol (1,25-Dihydroxycholecalciferol) Enhances Paclitaxel Antitumor Activity *in Vitro* and *in Vivo* and Accelerates Paclitaxel-induced Apoptosis," *Clinical Cancer Research*, (Apr. 2001) 7:1043-1051.

Hoikka, V. et al., "Treatment of Osteoporosis with 1-Alpha-Hydroxycholecalciferol and Calcium," *Acta. Med. Scand.*(1980) 207:221-224.

Holick, M.F. et al., *Proc. Natl. Acad. Sci. USA*, (1971) 68:803-804.

Holick, M.F. et al., *Science* (1973) pp. 180, 190-191.

Holick, M.F., "Noncalcemic Actions of 1,25-Dihydroxyvitamin $D_3$ and Clinical Applications", *Bone*, (1995) 17:2:107S-110S.

Horst et al., "Quantitation of Vitamin D and its Metabolites and Their Plasma Concentrations in Five Species of Animals," *Anal. Biochem.*, (1981) 116:189-203.

Horst et al., "Discrimination in the Metabolism of Orally Dosed Ergocalciferol and Cholecalciferol by the Pig, Rat and Chick," *Biochem. J.*, (1982) 204:185-189.

Jensen, G.F. et al., *Clin. Endocrinol.*, (1982) 16:515-524.

Johnson, C. et al. "Vitamin D-related Therapies in Prostate Cancer," *Cancer and Metastasis Review* 21, (2002) pp. 147-158.

Kanis, J.A. et al., "Guidelines for Clinical Trials in Osteoporosis, A Position Paper of the European Foundation for Osteoporosis," *Osteoporosis Int.*, (1991) 1:182-188.

Kim, S. et al., Potentiation of 1,25-Dihydroxyvitamin $D_3$-Induced Differentiation of Human Promyelocytic Leukemia Cells into Monocytes by Costunolide, a Germacranolide Sesquiterpene Lactone, *Biochem. Pharmacology*, (2002) 64:1233-1242.

Knutson, et al., "Metabolism of 1 α-Hydroxyvitamin $D_2$ to activated Dihydroxyvitamin $D_2$ Metabolites Decreases Endogenous 1α,25-Dihydroxyvitamin $D_3$ in Rats and Monkeys," *Endocrinology*, (1995) 136:11:4749-4753.

Kocienski, P.J. et al., "Calciferol and its Relatives. A Synthesis of Vitamin $D_4$," *J.C.S. Perkins I*, (1979) pp. 1290-1293.

Lam, H.Y. et al., *Science*, (1974) 486:1038-1040.

Londowski, J.M. et al., "Biological Activity of the C-1, C-3, C-25, β-D-Glucopyranosides of 1,25-Dihydroxyvitamin $D_3^1$," *J. Pharmacology Expr. Ther.*, (1986) 237:3:837-840.

Majewski, et al., "Inhibition of Tumor Cell-Induced Angiogenisis by Retinoids, 1,25-Dihydroxyvitamin $D_3$ and their Combination," *Cancer Letters*, (1993) 75:35-39.

Martin and DeLuca, "Calcium Transport," *Am. J. Physiol.*, 216:1352-1359.

Mathias, C.J. et al., "Tumor-Selective Radiopharmaceutical Targeting Via Receptor-Mediated Endocytosis of Gallium-67-Deferoxamine-Folate," *J. Nucl. Med.* (1996), 37(6):1003-1008.

McDonald, F.G., "The Multiple Nature of Vitamin D," *J. Biol. Chem.* 114, (1936) lxv.

*Merck Index*, S. Budavari (ed.), 11th ed., Merck & Co., Rahway, N.J. (1989) pp. 1579, #9930.

Miller et al., "The Human Prostatic Carcinoma Cell Line LNCaP Expresses Biologically Active, Specific Receptors for 1α,25-Dihydroxyvitamin $D_3^1$," *Cancer Res.*, (1992) 52:515-520.

Moffatt, K. et al., "1α,25-Dihydroxyvitamin $D_3$ and Platinum Drugs Act Synergistically to Inhibit the Growth of Prostate Cancer Cell Lines," *Clinical Cancer Research*, (Mar. 1999) 5:695-703.

Muindi, J. et al., "Pharmacokinetics of High-Dose Oral Calcitriol: Results From a Phase 1 Trial of Calcitriol and Paclitaxel," *Clinical Pharmacology & Therapeutics*, (Dec. 2002) pp. 648-659.

Nemeto, H. et al., "A Stereoselective Synthesis of 1 α—Hydroxy-Vitamin $D_3$," *Chemistry Letters*, (1985) 8:1131-1132.

Orimo, H. et al., "Reduced Occurrence of Vertebral Crush Fractures in Senile Osteoporosis Treated with 1α(OH)-Vitamin $D_3$," *Bone and Mineral*, (1987) 3:47-52.

Ott, S.M. and C.H. Chestnut, *Annals of Int. Med.*, (1989) 110:267-274.

Paaren et al., "Direct C(1) Hydroxylation of Vitamin $D_3$ and Related Compounds," *J. Org. Chem.*, (1980) 45:3253.

Packman, K. et al. "Combination Treatment of MCF-7 Xenografts with the Vitamin $D_3$ Analog EB1089 and Antiestrogens," (Vitamin D Endocrine Workshop, Nashville, TN May 27-Jun. 1, 2000) pp. 511-514.

Podenphant, J. et al., "Serum Bone Gla Protein and Other Biochemical Estimates of Bone Turnover in Early Postmenopausal Women During Prophylactic Treatment for Osteoporosis," *Acta Med Scand*, (1985) 218:329-333.

*Physicians's Desk Reference*, Edition 43:1746-1748.

Pouilles, J.M. et al., "Prevention of Early Postmenopausal Bone Loss with 1α-Hydroxy Vitamin $D_3$, A Three-Year Prospective Study," *Clin Rheumatol*. 11, 4 (1992) pp. 492-497.

Ravid, A. et al., "1,25-Dihydroxyvitamin $D_3$ Enhances the Susceptibility of Brease Cancer Cells to Doxorubicin-induced Oxidative Damage," *Cancer Research*, (Feb. 15, 1999) 59:862-867.

Reeve, L.E. et al., "Biological Activity of 1α—hydroxy Vitamin $D_2$ in the Rat," *Arch. Biochem. Biophys.* (Feb. 1978) 186:1:164-167.

Sato, F. et al., "Biological Activity of 1α,25-Dihydroxyvitamin D Derivatives—24-epi-1α,25-Dihydroxyvitamin D-2 and 1α,25-Dihydroxyvitamin D-7," Biochim. *Biophys. Acta*, (1991) 1091:188-192.

Shiraki, M. et al., *Endocrinol. Japan*, (1985) 32:305-315.

Siwinska, A. et al. "Potentiation of the Antiproliferative Effect *in Vitro* of Doxorubicin, Cisplatin and Genistein by New Analogues of Vitamin D," *Anticancer Research*, (2001) 21:1925-1929.

Sjoden et al., "Effects of 1 $OHD_2$ on Bone Tissue," *Acta. Endocrinol.* (Copenh.) (Aug. 1984) 16:4:564-568.

Sjoden, G. et al., "Antirachitic Activity of 1α-Hydroxyergocalciferol and 1α-Hydroxycholecalciferol in Rats," *J. Nutr.*, (1984) 114:2043-2046.

Sjoden, G. et al., "1α-Hydroxyvitamin $D_2$ is Less Toxic than 1α-Hydroxyvitamin $D_3$ in the Rat," *Proc. Soc. Exp. Biol. Med.*, (1985) 178:432-436.

Skowronski et al., "Actions Of Vitamin $D_3$ Analogs on Human Prostate Cancer Cell Lines: Comparison with 1,25-Dihydroxyvitamin $D_3$," *Endocrinology*, (1995) 136:20-26.

Skowronski et al., "Vitamin D and Prostate Cancer: 1,25 Dihydroxyvitamin $D_3$ Receptors and Actions in Human Prostate Cancer Cell Lines," *Endocrinology*, (1993) 132:1952-1960.

Slapak, C. et al., "Treatment of Acute Myeloid Leukemia in the Elderly with Low-Dose Cytarabine, Hydroxyurea, and Calcitriol," *Amer. J. Hematology*, (1992) 41:178-183.

Sommerfeldt et al., "Metabolism of Orally Administered [$^3$H]Ergocalciferol and [$^3$H]Cholecalciferol by Dairy Calves," *J. Nutr.*, (1983) 11:2595-2600.

Song, X.D. et al., "Bryostatin-1 and 1α,25-Dihydroxyvitamin $D_3$ Synergistically Stimulated the Differentiation of NB4 Acute Promyelocytic Leukemia Cells," *Leukemia*, (1999) 13:275-281.

Sorensen, O.H. et al., *Clin. Endocrinol.*, (1977) 7:169S-175S.

Studzinski, G. et al., "Potentiation by 1-α,25- Dihydroxyvitamin $D_3$ of Cytotoxicity to HL-60 Cells Produced by Cytarabine and Hydroxyurea," *J. National Cancer Inst.*, (Apr. 1986) 76:4:641-648.

Strugnell et al., "Metabolism of a Cyclopropane-Ring-Containing Analog of 1α-Hydroxyvitamin $D_3$ in a Hepatocyte Cell Model," *Biochem. Pharm.*, (1990) 40:333-341.

Strugnell et al., "1 α,24(S)-Dihydroxyvitamin $D_2$: a biologically active product of 1 α—hydroxyvitamin $D_2$ made in the human hepatoma, Hep3B," *Biochem. J.*, (1995) 310-233-241.

Suzuki, Y. et al., "The Enhancement of the Chemotherapeutic Effects on Human Prostate Cancer Cell—The Combination with the Growth Factor Interaction Inhibitor (Suramin)," *Acta Urologica* (1993) 12:1215-1220, (Abstract).

Swami, S. et al. "1α,25-Dihydroxyvitamin $D_3$ Down-Regulates Estrogen Receptor Abundance and Suppresses Estrogen Actions in MCF-7 Human Breast Cancer Cells," *Clinical Cancer Research*, (Aug. 2000) 6:3371-3379.

Tachibana, Y. (Nisshin Flour Milling Co.), "Preparation of 1Beta-Hydroxyvitamin $D_2$ and $D_3$," *Chemical Abstracts*, (1990) 113:1:6688 Col. 2 Abstract No. 6683y.

Tanaka, Y. et al., *Endocrinology* (1973) 92:417-422.

Torres, R. et al., Etoposide Stimulates 1,25-Dihydroxyvitamin $D_3$ Differentiation Activity, Hormone Binding and Hormone Receptor Expression in HL-60 Human Promyelocytic Cells, *Molecular and Cellular Biochemistry*, (2000) 208:157-162.

Tsuji, M. et al., "Synthesis of 22,23-Dihydro-1α,25-Dihydroxyvitamin $D_2$ and its 24R-Epimer, New Vitamin $D_2$ Derivatives," *Bull. Chem. Soc. Jpn.*, (1990) 63:8:2233-2238.

Wang, Q. et al., "1,25-Dihydroxyvitamin $D_3$ and All-trans-Retinoic Acid Sensitize Breast Cancer Cells to Chemotherapy-induced Cell Death," *Cancer Research*, (Apr. 2000) 60:2040-2048.

Wang, X. et al., "Inhibition of p38 MAP Kinase Activity Up-Regulates Multiple MAP Kinase Pathways and Potentiates 1,25-Dihydroxyvitamin $D_3$—Induced Differentiation of Human Leukemia HL60 Cells," *Experimental Cell Research*, (2000) 258:425-437.

Wientroub, S. et al. "The Dichotomy in the Effects of 1,25 Dihydroxy Vitamin $D_3$ and 24, 25 Dihydroxy Vitamin $D_3$ on Bone Gamma-Carboxyglutamic Acid-Containing Protein in Serum and Bone in Vitamin D-Deficient Rats," *Calcif, Tissue Int.*, (1987) 40:166-172.

Windaus, A. et al., "Uber das Krystallisierte Vitamin $D_4$," *Z. Physiol. Chem.*, (1937) 247:185-188.

Yu, W. et al., "Enhancement of 1,25- Dihydroxyvitamin $D_3$- Mediated Antitumor Activity with Dexamethasone," *J. National Cancer Inst.*, (Jan. 1998) 90:2:134-141.

Zerwekh et al., "Short-Term 1,25-Dihydroxyvitamin $D_3$ Administration Raises Serum Osteocalcin in Patients with Postmenopausal Osteoporosis," *J. Clin. Endocrinol. Metabol*, (1985) 60:615-617.

Abood et al., "Pharmacy Practice and the Law," (1994) pp. 27-28.

Parfitt, "Martindale, The Complete Drug Reference," (1999) pp. 1366-1369.

* cited by examiner

FORMULATION FOR LIPOPHILIC AGENTS

CROSS-REFERENCE TO RELATED APPLICATIONS

Not applicable.

STATEMENT REGARDING FEDERALLY SPONSORED RESEARCH OR DEVELOPMENT

Not Applicable

BACKGROUND OF THE INVENTION

This invention relates to pharmaceutical formulations of lipophilic therapeutic agents in which such agents are solubilized in largely aqueous vehicles, and uses for such formulations. The formulations are stable in aqueous-based vehicles, and have therapeutically and commercially useful concentrations of active ingredient.

Many pharmacologically active substances are lipophilic, i.e., only sparingly or negligibly water-soluble. Lipophilic therapeutic agents span the entire range of biologically and/or pharmacologically active substances. For example, they include certain analgesics and anti-inflammatory agents, anti-asthma agents, anti-bacterial agents, anti-viral agents, anti-coagulants, anti-depressants, anti-neoplastic agents and immunosuppressants, β-blockers, corticosteroids, opioid analgesics, lipid regulating agents, anxiolytics, sedatives, hypnotics and neuroleptics.

The poor water-solubility of these lipophilic agents often results in major difficulties in formulation, particularly when easily sterilizable and administrable homogeneous aqueous solutions are needed. Efficacious aqueous-based formulations are particularly problematic for systemic administration, in particular parenteral administration (i.e., injectable solutions) and for certain liquid preparations for, e.g., topical gynecologic, dermatologic ophthalmic, etc. use, and for use on the oral mucous membranes.

A number of approaches for obtaining aqueous compositions of sparingly water-soluble drugs are known. Such approaches seek to increase the solubility, and accordingly, increase the ease of formulation and the bioavailability of the sparingly soluble or lipophilic active agents. One such approach involves chemical modification of the lipophilic drug by introduction of a ionic or ionizable group or a group that lowers the melting point. The former generally depends upon the lipophilic drug having a hydroxyl or carboxy group which can be used to form various kinds of esters. The latter is based on the concept that, to be solubilized, the molecules have to leave the crystal lattice. Any modification of the molecule that lowers the melting point, and thus reduces the energy of the crystal lattice, tends to increase the solubility thereof in any solvent.

Another method involves physico-chemical solubilization techniques such as micellar solubilization by means of surface-active agents, i.e., the use of surfactant micelles to solubilize and transport the therapeutic agent. Micelles are agglomerates of colloidal dimensions formed by amphiphilic compounds under certain conditions. Micelles, and pharmaceutical compositions containing micelles, have been extensively studied and are described in detail in the literature. In aqueous solution, micelles can incorporate lipophilic therapeutic agents in the hydrocarbon core of the micelle, or can entangle the agents at various positions within the micelle walls. Although micellar formulations can solubilize a variety of lipophilic therapeutic agents, the loading capacity of conventional micelle formulations is limited by the solubility of the therapeutic agent in the micelle surfactant. For many lipophilic therapeutic agents, such solubility is too low to offer formulations that can deliver therapeutically effective doses.

The formation of complexes, solid solutions and solid dispersions by means of the use of suitable polymers is another approach for increasing the water-solubility of pharmaceutically active substances. In such a case, the active ingredient is incorporated in a suitable hydrophilic carrier, which increases the solubility and the bioavailability thereof without any formal covalent bonds originating between the drug and the polymer matrix. The difference between a solid solution and a solid dispersion is typically in the form of the active ingredient. In a solid solution, the active is present in the amorphous molecular form, while in a dispersion the active is present in a crystalline form, as fine as possible.

Even more widespread and studied is the use of the interaction between a polymer and a drug to give rise to a true complex, wherein chemical bonds of a noncovalent nature are involved. Complexing polymers employed in the pharmaceutical field include, e.g., polyethylene glycols, polypropylene glycols, cyclodextrins, carboxymethylcellulose, polyvinylpyrrolidone (PVP)

Co-precipitation is yet another widespread method for the preparation of complexes with increased solubility. In this method, the substance and the polymer are dissolved in an organic solvent in which they are both soluble, and the solution is then evaporated at atmospheric pressure, under vacuum, by spray-drying or by lyophilization, to yield a dry product actually made of the complex of the treated drug. Such complexes can also be obtained by applying other methods, such as grinding and mixing the ingredients in a mill, or by extrusion of a paste containing the two products together with a minor amount of water, etc. In comparison with the starting drug, the complex typically shows an appreciably enhanced water-solubility.

In devising a working method for solubilizing drugs by complexation, it is necessary to take into account the molecular weight of the polymer, since the solubility of the active ingredient directly depends thereon. In general, low molecular weights are more suitable than medium to high molecular weights.

Still another method involves use of various co-solvent systems, i.e., compositions using a solvent mixture containing water and one or more organic solvents. One approach to solubilizing lipophilic drug agents in aqueous systems is to employ some combination of alcohols and glycols (PDA J. Pharm. Sci. Technol. 50(5) 1996; U.S. Pat. Nos. 6,136,799; 6,361,758 and 5,858,999) Organic contents as high as 50% or more are often required to ensure solubility during manufacturing, storage and administration. Although organic levels while high will still be below the $LD_{50}$ for a low volume parenteral dosage, the amounts are still typically undesirable. High levels of organic solvent can cause pain on injection and tissue necrosis.

Other methods involve the formation of complexes by the addition of chelating agents such as citric acid, tartaric acid, amino acids, thioglycolic acid and edetate disodium. Others use buffering agents such as acetate, citrate, glutamate and phosphate salts. However, buffers and chelating agents have been implicated in imparting aluminum levels in products to in excess of 3.5 parts per million leading to adverse side effects. (International Patent Application Publication WO 96/36340) Moreover, certain chelating agents such as EDTA have be implicated in adverse effects such nephrotoxicity and renal tubular necrosis. (U.S. Pat. No. 6,361,758)

Each of these foregoing methods has its inherent limitations. For many of the pharmaceutical substances, the solubility levels that can be achieved with one or another of the methods discussed above are still insufficient to make their use in aqueous-based commercial products viable.

An exemplary and important class of lipophilic drug agents are the vitamin D compounds. Properly metabolized vitamin D compounds are necessary for the maintenance of healthy bones and have been found to display more other biological activities. The lipophilicity of the natural forms of vitamin D and of the many known synthetic analogs of vitamin D makes it difficult to manufacture an efficacious formulation, particularly, a parenteral formulation which is preferred for, e.g., renal dialysis patients.

Additionally, vitamin D compounds, among other lipophilic compounds, are known to be oxygen sensitive, being oxidized when exposed to air, and thus, losing integrity. One approach to circumventing this problem is to add an antioxidant directly to a formulation of the drug. However, certain antioxidants, such as ascorbic acid and sodium ascorbate, which are highly water soluble, will discolor in the course of performing their intended function. Buffers and/or chelating agents have also been added to decrease oxygen sensitivity thus maintaining active drug potency (U.S. Pat. Nos. 4,308,264; 4,948,788 and 5,182,274.) However, as noted above, buffers and chelating agents are known to introduce undesirable levels of aluminum into the product.

Thus, there is a need for pharmaceutical formulations of lipophilic therapeutic agents that overcome the limitations of the many known approaches.

BRIEF SUMMARY OF THE INVENTION

The present invention provides a pharmaceutical formulation that overcomes the problems associated with parenteral formulations of lipophilic drugs. The present invention provides a formulation that can be terminally sterilized, and contains little or no organic solvent such as alcohol. It has also been surprisingly discovered that the novel formulations of the present invention provide a synergistic solubilizing and antioxidative effect. Additionally, the present invention allows for the inclusion or occlusion of aseptic agents, depending on the intended use and/or handling.

The present invention provides a pharmaceutical formulation comprising a therapeutically effective amount of (1) a lipophilic therapeutic agent, (4) a non-ionic solubilizer, (3) a lipophilic antioxidant, and (4) optionally, an agent that is an organic solvent, or a preservative (e.g., antimicrobial), or both, in an aqueous vehicle. Lipophilic therapeutic agents suitable for use in the formulations of the present invention are not particularly limited. Agents of particular interest include vitamin D compounds and analogs. By employing a lipophilic, i.e., fat-soluble, antioxidant, smaller amounts of antioxidant may be used compared to known formulations utilizing water soluble antioxidants.

The formulations of the present invention preclude the need for high organic solvent contents, which can cause irritations in some patients. In addition, formulations of the present invention omit buffers and chelating agents. The use of buffers and chelating agents in, e.g., some prior vitamin D formulations, has been linked to the introduction of undesirable aluminum levels into the product and eventually into the patient.

The invention also relates to methods for the treatment and/or prophylaxis of certain diseases and disorders comprising administering, e.g., parenterally, to a patient in need thereof a formulation in accordance with the present invention. For example, for formulations containing vitamin D compounds or analogs, these diseases include hyperparathyroidism, e.g., secondary hyperparathyroidsim, neoplastic diseases, such as cancers of the pancreas, breast, colon or prostate as well as other diseases of abnormal cell differentiation and/or cell proliferation such as psoriasis, and disorders of calcium metabolism such as osteomalacia.

Other advantages and a fuller appreciation of the specific attributes of this invention will be gained upon an examination of the following detailed description of the invention, and appended claims.

BRIEF DESCRIPTION OF THE DRAWINGS

Not applicable.

DETAILED DESCRIPTION OF THE INVENTION

The present invention provides a stable, self-preserved pharmaceutical formulation of a lipophilic therapeutic agent in aqueous vehicle utilizing a non-ionic solubilizer and lipophilic antioxidant. The formulation is suitable for parenteral administration.

As used herein, "lipophilic" in reference to a therapeutic agent or drug is intended to mean a sparingly (or poorly, slightly, scarcely) soluble biologically active or pharmaceutically active substance or antigen-comprising material, which has a therapeutic or prophylactic effect, and has utility in the treatment or prevention of diseases or disorders affecting mammals, including humans, or in the regulation of an animal or human physiological condition. The water-solubility of lipophilic drugs, at room temperature, is typically too low to make commercially proposable, sufficiently active or advantageous any aqueous preparations containing the compound as an active ingredient. Lipophilic therapeutic agents include substances, typically compounds, with little or no water solubility. Intrinsic water solubilities (i.e., water solubility of the unionized form) for lipophilic therapeutic agents usable in-the present invention include, for example, those with a solubility of less than about 1% by weight, and typically less than about 0.1% or 0.01% by weight, or, e.g., less than about 10 µg/mL.

Lipophilic therapeutic agents suitable for use in the formulations of the present invention are not particularly limited, as the method of the present invention is surprisingly capable of solubilizing and delivering a wide variety of lipophilic therapeutic agents. Therapeutic agents that can be utilized with the formulations of the present invention may be selected from a wide range of biologically and/or pharmacologically active substances which lack adequate solubility in aqueous systems without a solubilizing agent. Such therapeutic agents include any agents having therapeutic or other value when administered to an animal, particularly to a mammal, such as drugs, prodrugs (i.e., agents than transform into active substances), nutrients (nutraceuticals), and cosmetics (cosmeceuticals). Such therapeutic agents can be utilized in formulations in accordance with the present invention so as to yield an effective therapeutic dose, e.g., for parenteral administration. The precise biological and/or pharmacological activity of the substance is immaterial, so long as the substance can be solubilized in the present formulations.

Specific non-limiting examples of lipophilic therapeutic agents that can be used in the formulations of the present invention include the following representative compounds, as well as their pharmaceutically acceptable salts, isomers, esters, ethers and other derivatives. These include:

analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenaminc acid, mefenamic acid, nabumetone, naproxen, oxaprozin, oxyphenbutazone, phenylbutazone, piroxicam, rofecoxib, sulindac, tetrahydrocannabinol, tramadol and tromethamine;

anthelmintics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-arrhythmic agents, such as amiodarone HCl, disopyramide, flecainide acetate and quinidine sulfate;

anti-asthma agents, such as zileuton, zafirlukast, terbutaline sulfate, montelukast, and albuterol;

anti-bacterial agents, such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

anti-viral agents, such as abacavir, amprenavir, delavirdine, efavirenz, indinavir, lamivudine, nelfinavir, nevirapine, ritonavir, saquinavir, and stavudine;

anti-coagulants, such as cilostazol, clopidogrel, dicumarol, dipyridamole, nicoumalone, oprelvekin, phenindione, ticlopidine, and tirofiban;

anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

anti-diabetic agents, such as acetohexamide, chlorpropamide, glibenclamide, gliclazide, glipizide, glimepiride, miglitol, pioglitazone, repaglinide, rosiglitazone, tolazamide, tolbutamide and troglitazone;

anti-epileptic agents, such as beclamide, carbamazepine, clonazepam, thotoin, felbamate, fosphenytoin sodium, lamotrigine, methoin, methsuximide, methylphenobarbitone, oxcarbazepine, paramethadione, phenacemide, phenobarbitone, phenytoin, phensuximide, primidone, sulthiame, tiagabine HCl, topiramate, valproic acid, and vigabatrin;

anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid;

anti-gout agents, such as allopurinol, probenecid and sulphinpyrazone;

anti-hypertensive agents, such as amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

anti-malarial agents, such as amodiaquine, chloroquine, chlorproguanil HCl, halofantrine HCl, mefloquine HCl, proguanil HCl, pyrimethamine and quinine sulfate;

anti-migraine agents, such as dihydroergotamine mesylate, ergotamine tartrate, frovatriptan, methysergide maleate, naratriptan HCl, pizotifen maleate, rizatriptan benzoate, sumatriptan succinate, and zolmitriptan;

anti-muscarinic agents, such as atropine, benzhexol HCl, biperiden, ethopropazine HCl, hyoscyamine, mepenzolate bromide, oxyphencyclimine HCl and tropicamide;

anti-neoplastic agents and immunosuppressants, such as aminoglutethimide, amsacrine, azathioprine, bicalutamide, bisantrene, busulfan, camptothecin, capecitabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate;

anti-protozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole;

anti-thyroid agents, such as carbimazole and propylthiouracil;

anti-tussives, such as benzonatate;

anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, risperidone, sertindole, sulpiride, temazepam, thioridazine, triazolam, zolpidem, and zopiclone;

β-blockers, such as acebutolol, alprenolol, atenolol, labetalol, metoprolol, nadolol, oxprenolol, pindolol and propranolol;

cardiac inotropic agents, such as anrinone, digitoxin, digoxin, enoximone, lanatoside C and medigoxin;

corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

diuretics, such as acetazolamide, amiloride, bendroflumethiazide, bumetanide, chlorothiazide, chlorthalidone, ethacrynic acid, frusemide, metolazone, spironolactone and triamterene;

anti-parkinsonian agents, such as bromocriptine mesylate, lysuride maleate, pramipexole, ropinirole HCl, and tolcapone;

gastrointestinal agents, such as bisacodyl, cimetidine, cisapride, diphenoxylate HCl, domperidone, famotidine, lanosprazole, loperamide, mesalazine, nizatidine, omeprazole, ondansetron HCl, rabeprazole sodium, ranitidine HCl and sulphasalazine;

histamine $H_1$ and $H_2$-receptor antagonists, such as acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

keratolytics, such as acetretin, calciprotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, fenofibrate, fluvastatin, gemfibrozil, pravastatin, probucol, and simvastatin;

muscle relaxants, such as dantrolene sodium and tizanidine HCl;

nitrates and other anti-anginal agents, such as amyl nitrate, glyceryl trinitrate, isosorbide dinitrate, isosorbide mononitrate and pentaerythritol tetranitrate;

nutritional agents and fat-soluble vitamins, such as calcitriol, carotenes, dihydrotachysterol, essential fatty acids, non-essential fatty acids, phytonadiol, vitamin A, vitamin $B_2$, vitamin D, vitamin E and vitamin K;

opioid analgesics, such as codeine, dextropropoxyphene, diamorphine, dihydrocodeine, fentanyl, meptazinol, methadone, morphine, nalbuphine and pentazocine;

sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone;

stimulants, such as amphetamine, dexamphetamine, dexfenfluramine, fenfluramine and mazindol;

and others, e.g., erectile dysfunction improvement agents, anti-osteoporosis agents, anti-obesity agents, cognition enhancers, anti-urinary incontinence agents, anti-benign prostate hypertrophy agents, such as becaplermin, donepezil HCl, L-thryroxine, methoxsalen, verteporfin, physostigmine, pyridostigmine, raloxifene HCl, sibutramine HCl, sildenafil citrate, tacrine, tamsulosin HCl, and tolterodine.

It should be appreciated that this listing of lipophilic therapeutic agents and their therapeutic classes is merely illustrative. Indeed, a particular feature, and surprising advantage, of the formulations of the present invention is the ability of the present formulations to solubilize and deliver a broad range of lipophilic therapeutic agents, regardless of functional class. Of course, mixtures of lipophilic therapeutic agents may also be used where desired.

Examples of lipophilic agents of particular interest include active vitamin D compounds. As used herein, the term "activated vitamin D" or "active vitamin D" is intended to include any biologically active vitamin D compound, including a pro-drug (or pro-hormone), a precursor, a metabolite or an analog, in any stage of its metabolism. It is known that vitamin D compounds display a variety of biological activities, e.g., in calcium and phosphate metabolism (see, e.g., U.S. Pat. No. 5,104,864), as an antineoplastic agent (see, e.g., U.S. Pat. No. 5,763,429), and as an antihyperparathyroid agent (see, e.g., U.S. Pat. No. 5,602,116), and it is contemplated that any of the biologically active forms of vitamin D can be used in the formulations in accordance with the present invention. Generally, an active vitamin D compound or analog is hydroxylated in at least the C-1, C-24 or C-25 position of the molecule, and either the compound itself or its metabolite binds to the vitamin D receptor (VDR). Pro-drugs, for example, include vitamin D compounds that are hydroxylated in the C-1. Such compounds undergo further hydroxylation in vivo and their metabolites bind the VDR.

Precursors include previtamins, such as $1\alpha$-hydroxyprevitamin $D_2$, $1\alpha,24$-dihydroxyprevitamin $D_2$, $1\alpha,25$-dihydroxyprevitamin $D_2$, 24-hydroxyprevitamin $D_2$, $1\alpha$-hydroxyprevitamin $D_3$ and $1\alpha,25$-dihydroxyprevitamin $D_3$, which are thermal isomeric forms of the vitamin forms. Metabolites generally include compounds or analogs that have undergone further metabolic processing, e.g., hydroxylation.

Examples of vitamin D compounds suitable for formulations of the present invention include, without limitation, $1\alpha,24$-dihydroxyvitamin $D_2$, $1\alpha,2$-dihydroxyvitamin $D_4$, $1\alpha,24$-dihydroxyvitamin $D_2$, $1\alpha,25$-dihydroxyvitamin $D_3$ (calcitriol), $1\alpha$ hydroxyvitamin $D_3$ ($\alpha$-calcidol) $1\alpha,25$-dihydroxyvitamin $D_2$, $1\alpha,25$-dihydroxyvitamin $D_4$, and $1\alpha,24,25$-dihydroxyvitamin $D_2$, seocalcitol (EB-1089), calcipotriol, 22-oxacalcitrol (maxacalcitol), fluorinated compounds such as falecalcitriol, and 19-nor compounds such as paricalcitol. Among those compounds having a chiral center, e.g., in the sidechain, such as at C-24, it is understood that both epimers (e.g., R and S) and the epimeric mixture are within the scope of the present invention.

It also is understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

The amount of selected therapeutic is not critical to the present invention and may be varied to achieve the desired therapeutic response for a particular patient. The amount of active therapeutic agent in the formulations of the invention will be dependent, in part, on the solubility of the specific surfactant used and its intended use. Those skilled in the arts can adjust the ratios without undue experimentation. The selected dosage also will depend on the activity of the specific therapeutic, the route of administration, the severity of the condition being treated and the condition and history of the specific patient. For example, a therapeutic dose for vitamin D-type compounds may range between about 2 µg and about 100 µg/dose.

Suitable solubilizing agents for the formulations of the present invention include nonionic solubilizers. A non-ionic solubilizer is one where the hydrophilic part of the solubilizer carries no charge but derives its water solubility from highly polar groups such as hydroxyl or polyoxyethylene groups. Some surfactants known for use in the pharmaceutical field also have a solubilizing function.

Solubilizers generally include, but are not limited to, the polyoxyalkylenes dextrans, fatty acid esters of saccharose, fatty alcohol ethers of oligoglucosides (e.g., the akylpolyglucosides such as TRITON™), fatty acid esters of glycerol (e.g., glycerol mono/distearate or glycerol monolaurate), and polyoxyethylene type compounds (e.g., POE, PEG, PEO, SOLUTOL™ CREOMOPHOR™S, MACROGOL, CARBOWAX, POLYOXYL). The latter also include polyethoxylated fatty acid esters of sorbitan (e.g., polysorbates, such as TWEEN™s, SPAN™s), fatty acid esters of poly (ethylene oxide) (e.g., polyoxyethylene stearates), fatty alcohol ethers of poly(ethylene oxide) (e.g., polyoxyethylated lauryl ether), alkylphenol ethers of poty(ethylene oxide) (e.g., polyethoxylated octylphenol), polyoxyethylene-polyoxypropylene block copolymers (also known as poloxamers, such as "Pluronic"), and ethoxylated fats and oils (e.g., ethoxylated castor oil, or polyoxyethylated castor oil, also known as polyethylene glycol-glyceryl triricinoleate). Mixtures of solublilizers are also within the scope of the invention. Such mixtures are readily available from standard commerical sources. Solubilizers of particular interest include polysorbates, e.g. TWEEN™. Amounts of such solubilizer present in the formulations of the present invention include from about 0.05% to about 5% w/w.

Suitable lipophilic antioxidants include, but are not limited to, butylated hydroxytoluene (BHT), lipoic acid, lycopene, lutein, lycophyll, xanthophyll, carotene, zeaxanthin or vitamin E and/or esters thereof. The lipophilic antioxidants are present in very small but effective amounts, e.g., about 20 to about 2000 ppm.

If desired, formulations of the present invention can optionally include additional agents to enhance the solubility of the lipophilic therapeutic agent in the carrier system. Examples of such optional agents include organics solvents, preservatives or both. Such agents include alcohols and polyols, such as ethanol, benzyl alcohol, chlorobutanol, isopropanol, butanol, ethylene glycol, propylene glycol, butanediols, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives. Amounts of optional agents include 0% to about 30% w/w, e.g., organic solvent. A useful range is 0% to about 10% w/w, and a particularly useful range is about 1% to about 3%.

Accordingly, a formulation in accordance with the present invention includes a lipophilic drug agent (e.g., a drug agent with a solubility in water of <10 μg/mL), about 0.05% to about 5% w/w of a non-ionic solubilizer, about 20 to about 2000 ppm lipophilic antioxidant, and 0% to about 30% w/w optional agent. A particular formulation for treating secondary hyperparathyroidism includes 2–6 μg/mL 1α-hydroxyvitamin $D_2$ (doxercalciferol), 2.5% w/w benzyl alcohol, 0.5%–2.5% w/w TWEEN™-20, and 20 ppm BHT. The amount of optional agent, e.g., benzyl alcohol or ethanol, may range from 0 to 30% w/w; a highly useful range comprises 1% to 3% w/w. With a vitamin D formulation (e.g., a doxercalciferol formulation), a most useful amount of optional agent comprises 2.5% w/w.

A pharmaceutical formulation in accordance with the present invention comprises an aqueous vehicle. The aqueous vehicle contains, of course, water, but it may furthermore also contain pH adjusting agents, stabilizing agents, solubilizing agent (see, hereinabove), isotonic adjusting agents, and solvents (e.g. organic solvents; as discussed above). A formulation in accordance with the present invention precludes the need for high organic solvent which can cause irritation in some patients. In some cases, however, it may be appropriate to include an organic solvent or co-solvents. The amount of water in a formulation in accordance with the present invention is normally at least about from about 50% to about 99% w/w.

For the pharmaceutical formulations of the present invention, the intended route of administration is suitably parenteral, i.e., for use by injection into, e.g., an animal or human body. Such route includes intravenous, intramuscular and subcutaneous administration, the intravenous route being especially suitable for the formulations of the present invention for use in connection with, e.g., secondary hyperparathyroidism or neoplastic disorders.

However, whenever relevant, formulations in accordance with the present invention may also be suitable for use by other administration routes such as, e.g., the oral route, the topical route or the nasal route. In such cases, a person skilled in the art can make any necessary adjustments with respect to the concentration of the active substance and with respect to the other ingredients included in the formulation.

A formulation in accordance with the present invention is normally presented as an aqueous solution. However, in certain cases such as, e.g., in connection with the administration of a formulation by the topical or oral route, a formulation in accordance with the present invention may include a liquid composition which may be presented in the form of a solution or a gel.

Pharmaceutical formulations may be readily prepared by using pharmacopoeia grade reagents in which the reagents are made up in stock solutions from which the resulting solutions at the appropriate concentrations can be made. Once the appropriate amounts of stock solution and combined, it is often desirable to stir the reagents for several minutes under nitrogen gas gently blown over the top of the mixture, i.e., a nitrogen gas overlay. Degassed Water for Injection is then added to bring the desired final volume, and stirring under nitrogen gas continued for another several minutes.

A pharmaceutical formulation in accordance with the present invention containing a vitamin D compound or a vitamin D analogue like those substances described above, is suitable for use in the treatment and/or prophylaxis of (i) diseases or conditions characterized by abnormal cell differentiation and/or cell hyperproliferation such as, e.g., psoriasis and other disturbances of keratinisation, neoplastic diseases and cancers, such as pancreas, breast, colon and prostate cancers as well as skin cancer; (ii) diseases of, or imbalance in, the immune system, such as host-versus-graft and graft-versus-host reaction and transplant rejection, and auto-immune diseases such as discoid and systemic lupus erythematosus, diabetes mellitus and chronic dermatoses of auto-immune type, e.g., scleroderma and pemphigus vulgaris; (iii) inflammatory diseases such as rheumatoid arthritis as well as in the treatment and/or prophylaxis of a number of (iv) other diseases or disease states, including hyperparathyroidism, particularly secondary hyperparathyroidism associated with renal failure, and in promoting (v) osteogenesis and treating/preventing bone loss as in osteoporosis and osteosmalacia. (For use of vitamin D compounds for treatment and prophylaxis, see, e.g., U.S. Pat. Nos. 5,9722, 917; 5,798,345; 5,763,428; 5,602,116; 5,869,386; 5,104, 864; 5,403,831; 5,880,114; 5,561,123. The vitamin D formulations in accordance with the present invention are especially suited for treatment of cell hyperproliferative disorders; disorders of the calcium metabolism, such as osteomalacia; or neoplastic diseases, such as cancers of the pancreas, breast, colon or prostate. The method of treatment comprises treating the cells and/or administering to a patient in need thereof a formulation in accordance with the present invention in an amount that is effective to amelariate or prevent the disease or disorder. For example, in the treatment of hyperproliferative or neoplastic diseases, an effective amount is, e.g., a growth-inhibiting amount. Daily dosages as well as episodic doses, e.g., once per week to three times per week, are contemplated.

Additionally, as described hereinabove, vitamin D compounds in accordance with the present invention include prodrugs, i.e., drugs that require further metabolic processing in vivo, e.g., additional hydroxlation. Such prodrugs of vitamin D compounds that have been found to be effective therapeutic agents are generally less reactive than, e.g., the dihydroxy natural hormone, 1α,25-dihydroxyvitamin $D_3$. These compounds may offer further advantage for use in formulations.

In addition, formulations of the current invention may be terminally sterilized by means of e.g., autoclaving.

The present invention is further explained by the following examples which should not be construed by way of limiting the scope of the present invention.

Preparation of Stock Solutions

EXAMPLE 1

Doxercalciferol (1α-hydroxyvitamin $D_2$) Stock Solution 12.558 mg of doxercalciferol was weighed and transferred to a 10-mL volumetric flask. The solid was diluted to volume with ethanol and the flask was vigorously shaken to dissolve the solid.

EXAMPLE 2

Butylated Hydroxytoluene (BHT) Stock Solution 2.22 g BHT was transferred to a 100-mL volumetric flask. The solid was diluted to volume with ethanol and the flask was vigorously shaken to dissolve the solid.

EXAMPLE 3

10% TWEEN™-20

100 g TWEEN™-20KR was transferred to a 1-L volumetric flask and diluted to volume with degassed Water for Injection. A magnetic stir bar was added and the mixture stirred to mix.

Formulations

EXAMPLE 4

Doxercalciferol Formulations

The general procedure for preparing doxercalciferol formulations was as follows. To a glass formulation vessel was added Doxercalciferol Stock Solution, 10% TWEEN™-20, BHT Stock Solution, and ethanol, in the order listed. Nitrogen gas was gently blown over the top of the mixture. A stir bar was added to the mixture and stirred for not less than 20 minutes while continuing the nitrogen gas overlay. Degassed Water for Injection was added to bring the final volume to one liter. The mixture was stirred for not less than 20 minutes while continuing the nitrogen gas overlay. The volumes of each component used in preparing the formulations are listed in the Table 1 below.

TABLE 1

Preparation of Doxercalciferol Formulations

| Doxercalciferol Stock (mL) | Tween ™-20 Stock (mL) | BHT Stock (mL) | Ethanol (mL) | Water for Injection (mL) |
|---|---|---|---|---|
| 2.0 | 50 | 1.0 | 27 | 920 |
| 6.0 | 250 | 1.0 | 23 | 720 |

Use of Formulations

EXAMPLE 5

Double-Blind Study in End Stage Renal Disease (ESRD) Patients Exhibiting Secondary Hyperparathyroidism Up to 120 ESRD (End Stage Renal Disease) patients undergoing chronic hemodialysis are studied in a multicenter, double-blind, placebo-controlled study based in two major U.S. metropolitan areas. The selected patients reside in two major metropolitan areas within the continental U.S., have ages between 20 and 75 years and have a history of secondary hyperparathyroidism. They have been on hemodialysis for at least four months, have a normal (or near normal) serum albumin, and have controlled serum phosphorus (often by using oral calcium phosphate binders).

On admission to the study, each patient is assigned at random to one of two treatment groups. One of these groups receives two consecutive 12-week courses of therapy with 1α-OH-vitamin $D_2$ (doxercalciferol); the other receives a 12-week course of therapy with 1α-OH-vitamin $D_2$ followed, without interruption, by a 12-week course of placebo therapy. Each patient discontinues any 1, α,25-$(OH)_2$-vitamin $D_3$ therapy for eight weeks prior to initiating 1α-OH-vitamin $D_2$ therapy (daily dose of 4 μg doxercalciferol, formulated with 2.5% w/w benzyl alcohol, 0.5%–2.5% w/w TWEEN™-20, and 20 ppm BHT). Throughout this eight-week washout (or control) period and the two subsequent 12-week treatment periods, patients are monitored weekly for serum calcium and phosphorus. Serum intact PTH is monitored weekly or biweekly, and bone-specific serum markers, serum vitamin D metabolites, serum albumin, blood chemistries, hemoglobin and hematocrit are monitored at selected intervals.

During the study, patients undergo routine hemodialysis (three times per week) using a 1.24 mM calcium dialysate and ingest calcium phosphate binders (such as calcium carbonate or calcium acetate) in an amount sufficient to keep serum phosphate controlled (6.9 mg/dL). Patients who develop persistent mild hypercalcemia or mild hyperphosphatemia during the treatment periods reduce their 1α-OH-vitamin $D_2$ to 4 μg three times per week (or lower). Patients who develop marked hypercalcemia or marked hyperphosphatemia immediately suspend treatment. Such patients are monitored at twice weekly intervals until the serum calcium or phosphorus is normalized, and resume 1α-OH-vitamin $D_2$ dosing at a rate which is 4 μg three times per week (or lower).

During the eight-week washout period, the mean serum level of PTH increases progressively and significantly. After initiation of 1α-OH-vitamin $D_2$ dosing, mean serum PTH decreases significantly to less than 50% of pretreatment levels. Due to this drop in serum PTH, some patients need to reduce their dosage of 1α-OH-vitamin $D_2$ to 4 μg three times per week (or to even lower levels) to prevent excessive suppression of serum PTH. In such patients, exhibiting excessive suppression of serum PTH, transient mild hypercalcemia is observed, which is corrected by appropriate reductions in 1α-OH-vitamin $D_2$ dosages.

At the end of the first 12-week treatment period, mean serum PTH is in the desired range of 130 to 240 μg/mL and serum levels of calcium and phosphorus are normal or near normal for end stage renal disease patients. At the end of the second 12-week treatment period (during which time 1α-OH-vitamin $D_2$ treatment is suspended and replaced by placebo therapy), mean serum PTH values markedly increase, reaching pretreatment levels. This study demonstrates that: (1) 1α-OH-vitamin $D_2$ is effective in reducing serum PTH levels, and (2) 1α-OH-vitamin $D_2$ is safer than currently used therapies, despite its higher dosages and concurrent use of high levels of oral calcium phosphate binder.

EXAMPLE 6

Open Label Study of Elderly Subjects with Elevated Blood PTH from Secondary Hyperparathyroidism Thirty elderly subjects with secondary hyperparathyroidism are enrolled in an open label study. The selected subjects have ages between 60 and 100 years and have elevated serum PTH levels (greater than the upper limit of young normal range). Subjects also have femoral neck osteopenia (femoral neck bone mineral density of 0.70 μg/cm²).

Subjects are requested to keep a diet providing approximately 500 mg calcium per day without the use of calcium supplements. For a twelve week treatment period, subjects self-administer orally 2.5 μg/day 1α-OH-vitamin $D_2$.(i.e., 2.5 μg doxercalciferol, 2.5% w/w benzyl alcohol, 0.5%–2.5% w/w TWEEN™-20, and 20 ppm BHT) At regular intervals throughout the treatment period, subjects are monitored for serum PTH levels, serum calcium and phosphorus, and urine calcium and phosphorus levels. Efficacy is evaluated by pre- and post-treatment comparisons of serum PTH levels. Safety is evaluated by serum and urine calcium and phosphorus values.

The administration of 1α-OH-vitamin $D_2$ is shown to significantly reduce PTH levels with an insignificant incidence of hypercalcemia, hyperphosphatemia, hypercalciuria and hyperphosphaturia.

EXAMPLE 7

Clinical Studies of 1α,24-$(OH)_2D_2$ in Treatment of Prostate Cancer

Patients with advanced androgen-independent prostate cancer participate in an open-labeled study of 1α,24-$(OH)_2D_2$. Qualified patients are at least 40 years old, exhibit histologic evidence of adenocarcinoma of the prostate, and present with progressive disease which had previously responded to hormonal intervention(s). On admission to the study, patients begin a course of therapy with intravenous 1α,24-$(OH)_2D_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily 1α,24-$(OH)_2D_2$ is determined by administering progressively higher dosages to successive groups of patients. All doses are administered in the morning before breakfast. The first group of patients is treated with 25.0 μg of 1α,24-$(OH)_2D_2$ (formulated with 2.5% w/w benzyl alcohol, 0.5%–2.5% w/w TWEEN™-20, and 20 ppm BHT). Subsequent groups of patients are treated with 50.0, 75.0 and 100.0 μg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 μg.

Results from the first phase of the study show that the MTD for 1α,24-$(OH)_2D_2$ is above 20.0 μg/day, a level which is 10- to 40-fold higher than can be achieved with 1α,25-$(OH)_2D_2$. Analysis of blood samples collected at regular intervals from the participating patients reveal that the levels of circulating 1α,24-$(OH)_2D_2$ increase proportionately with the dosage administered, rising to maximum levels well above 100 pg/mL at the highest dosages, and that circulating levels of 1α,25-$(OH)_2D_2$ are suppressed, often to undetectable levels. Serum and urine calcium are elevated in a dose responsive manner. Patients treated with the MTD of 1α,24-$(OH)_2D_2$ for at least six months report that bone pain associated with metastatic disease is significantly diminished.

During the second phase, patients are treated with 1α,24-$(OH)_2D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 8

1α-$(OH)D_2$

The study of Example 7 is repeated for the active vitamin D compound, 1α-$(OH)D_2$ (formulated with 2.5% w/w benzyl alcohol, 0.5%–2.5% w/w TWEEN™-20, and 20 ppm BHT). The results of the phase one study indicate that patients treated with the MTD of 1α-$(OH)D_2$ for at least six months report that bone pain associated with metastatic disease is significantly diminished. The results of the phase two study indicate that after two years, CAT scans, X-rays and bone scans used for evaluating the progression of metastatic disease show stable disease or partial remission in many patients treated at the lower dosage, and stable disease and partial or complete remission in many patients treated at the higher dosage. In summary, the present invention provides an improved formulation for lipophilic drug agents that are only slightly soluble in an aqueous vehicle. The formulation in addition to the lipophilic drug agent includes a lipophilic antioxidant, a non-ionic solubilizer or surfactant, and optionally, an agent which is an organic solvent/ preservative.

All patents, publications and references cited herein are hereby fully incorporated by reference. In the case of conflict between the present disclosure and the incorporated patents, publications and references, the present disclosure should control.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

The invention claimed is:

1. A parenteral formulation, comprising a lipophilic drug which is doxercalciferol, a non-ionic solubilizer which is polysorbate 20 present at a concentration of about 0.05% to about 5% w/w, a lipophilic antioxidant which is butylated hydroxytoluene (BHT) present at a concentration of about 20 to about 2000 ppm, an optional agent which is ethanol present at a concentration of 0 to 30% w/w, and an aqueous vehicle.

2. A formulation as set forth in claim 1, wherein the optional agent is present in a concentration of 0% to about 10% w/w.

3. A formulation as set forth in claim 1, wherein the optional agent is present in a concentration of about 1% to about 3% w/w.

4. A formulation as set forth in claim 1, wherein the non-ionic solubilizer includes 0.5%–2.5% w/w polysorbate 20, the lipophilic antioxidant includes 20 ppm BHT and the optional agent includes 2.5% w/w ethanol.

5. A formulation as set forth in claim 1, wherein the doxercalciferol is present at a concentration of 2–10 μg/mL.

6. A parenteral formulation suitable for treatment of secondary hyperparathyroidism comprising 2–10 μg/mL of doxercalciferol 0.5%–2.5% w/w polysorbate 20, 20 ppm BHT and 2.5% w/w ethanol.

* * * * *

(12) INTER PARTES REEXAMINATION CERTIFICATE (0440th)
United States Patent
Mazess et al.

(10) Number: US 7,148,211 C1
(45) Certificate Issued: Aug. 28, 2012

(54) FORMULATION FOR LIPOPHILIC AGENTS

(75) Inventors: Richard B. Mazess, Madison, WI (US); Jeffrey W. Driscoll, Middleton, WI (US); Creighton Reed Goldensoph, DeForest, WI (US); Leon W. LeVan, Oregon, WI (US)

(73) Assignee: Genzyme Corporation, Cambridge, MA (US)

Reexamination Request:
No. 95/001,245, Oct. 13, 2009

Reexamination Certificate for:
Patent No.: 7,148,211
Issued: Dec. 12, 2006
Appl. No.: 10/247,765
Filed: Sep. 18, 2002

(51) Int. Cl.
*A01N 45/00* (2006.01)
*A61K 9/00* (2006.01)
*A61K 31/59* (2006.01)
*A61K 31/592* (2006.01)
*A61K 47/10* (2006.01)
*A61K 47/26* (2006.01)

(52) U.S. Cl. ........................................ 514/168; 514/167

(58) Field of Classification Search ........................ None
See application file for complete search history.

(56) References Cited

To view the complete listing of prior art documents cited during the proceeding for Reexamination Control Number 95/001,245, please refer to the USPTO's public Patent Application Information Retrieval (PAIR) system under the Display References tab.

*Primary Examiner* — Evelyn Huang

(57) ABSTRACT

The invention relates to pharmaceutical formulations of lipophilic therapeutic agents in which such agents are solubilized in largely aqueous vehicles, and processes for preparing and using the same.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *